United States Patent [19]
Buchner

[11] 4,161,122
[45] Jul. 17, 1979

[54] APPARATUS FOR EXAMINING BODIES THROUGH SCANNING BY MEANS OF ULTRASOUND

[75] Inventor: Klaus Buchner, Uttenreuth, Fed. Rep. of Germany

[73] Assignee: Siemens Aktiengesellschaft, Berlin & Munich, Fed. Rep. of Germany

[21] Appl. No.: 919,826

[22] Filed: Jun. 28, 1978

[30] Foreign Application Priority Data

Jul. 27, 1977 [DE] Fed. Rep. of Germany ....... 2733920

[51] Int. Cl.$^2$ ............................................. G01N 29/04
[52] U.S. Cl. ...................................... 73/626; 128/660
[58] Field of Search ................. 73/626, 628; 128/2 V; 340/1 R

[56] References Cited

U.S. PATENT DOCUMENTS 4,064,741  12/1977  Reynolds ............................... 73/626

*Primary Examiner*—Anthony V. Ciarlante
*Attorney, Agent, or Firm*—Hill, Van Santen, Steadman, Chiara & Simpson

[57] ABSTRACT

The illustrated apparatus comprises an ultrasonic array and an actuating system for actuating the transducer elements of the array in groups with an alternating number of transducer elements. Actuation proceeds, in an interlaced transmission/receiving cadence, in groups with an even-numbered and in groups with an odd-numbered count of transducer elements such that each connected even-numbered and odd-numbered group, in relation to the previously connected group, is, in a first clock interval, first receiver for the echo signals of the transmission beam of the preceding group, and, in a following clock interval, is switched over to transmission. The apparatus is used particularly in electromedical ultrasonic sectional image diagnosis.

8 Claims, 5 Drawing Figures

APPARATUS FOR EXAMINING BODIES THROUGH SCANNING BY MEANS OF ULTRASOUND

BACKGROUND OF THE INVENTION

The invention relates to an apparatus for examining bodies through scanning by means of ultrasound comprising an ultrasonic applicator consisting of at least one row of adjacently disposed ultrasonic transducer elements and an actuating system for the purpose of actuating the transducer elements individually or in groups, whereby the actuating system for actuating the transducer elements of the ultrasonic applicator is constructed in such symmetrical configurations with an even-numbered and an odd-numbered count of transducer elements that the symmetry axes of the configurations of simultaneously energized transducer elements, at one time, become placed in the gaps between two adjacent transducer elements, and, at another time, in the centers of the transducer elements, whereby the actuation proceeds in such a manner that, in the course of the scanning cycle over the entire length of the applicator, the symmetry axes occupy, at least once, every possible position in the gaps between the two transducer elements, and in the centers of the transducer elements, respectively, with the possible exception of only the transducer elements of the first half of the first, and the second half of the last transducer element group of the applicator.

In the apparatus according to the U.S. application Ser. No. 799,970, the complete sequential pulsing cycle of the transducer elements of the ultrasonic array (e.g. according to FIG. 2) proceeds, in a predetermined scanning pattern, in groups with a higher and in groups with a lower number of transducer elements, whereby each connected group, in unchanged formation, is both transmitter as well as receiver of the echo signals of the ultrasonic pulses expressly radiated by this group. Thus, since switching over takes place, in the cadence of additional transmitting/receiving cycles, between groups with a higher and lower number of transducer elements, the sonic field travel path in the object to be examined varies according to the clock pulse of the transmitting-/receiving cycles, and varying echo intensities are obtained per ultrasonic scan line. However, conditioned by this effect, echo pulses of a homogeneous boundary layer are recorded on the viewing screen of a cathode ray tube which has been brightness (or light intensity) modulated by the echos, said echo pulses being recorded thereon as a structure with varying brightness (or light intensity).

SUMMARY OF THE INVENTION

It is the object of the invention to construct the apparatus of the aforementioned prior application with the least technical outlay such that homogeneous echo structures are recorded with a uniform light intensity on the viewing screen of the cathode-ray tube.

In accordance with the invention, the object is achieved by virtue of the fact that, by means of the actuating system, in an interlaced (or interleaved) transmit/receive cadence, groups having an even-numbered and groups having an odd-numbered count of transducer elements are connected in a chronologically interlaced fashion such that each connected even-numbered or odd-numbered group, in relation to the previously connected group, in a first clock pulse, is first receiver for the echo signals of the transmitting beam of the preceding group, and, in a subsequent clock pulse, is switched over to transmission.

In the apparatus according to the invention, switching over is indeed carried out between groups of any desired numbers. However, the switching over proceeds in such a manner that, although transmission is carried out with one group having a specified number of transducer elements, subsequent reception is carried out with an additional group having a different number of transducer elements, respectively. This additional group then simultaneously forms the transmitting group for the following cycle whereby, however, for the purpose of receiving, following the transmitting pulse of this additional group, a switching over is again effected to a group having a different number of transducer elements; e.g. having a number of that particular group which was initially switched on. The active transducer elements act as acoustic radiators, respectively, whereby, in accordance with the reciprocity theorem, transmitting and receiving arrays can be interchanged, such that, for each transmitting/receiving cycle, approximately equal transmitting/receiving conditions are obtained. Thus, however, essentially equally great intensities result for the echo pulses of all ultrasonic lines. The echo visual image on the viewing screen of the cathode ray tube thus consists of points of constant (or uniform) brightness (or light intensity) for homogeneous boundary layers. In a preferred embodiment of the apparatus according to the invention, the actuating system is intended to alternately connect, in a chronologically interlaced fashion, groups having an even-numbered and groups having an odd-numbered count of transducer elements, whereby each connected even-numbered or odd-numbered group, in relation to the previously connected odd-numbered or even-numbered group, respectively, is first receiver and then again transmitter.

Further advantages and details of the invention shall be apparent from the following description of a sample embodiment on the basis of the accompanying sheets of drawings in conjunction with the subclaims; and other objects and features will be apparent from this detailed disclosure and from the appended claims.

BRIEF DESCRIPTION OF THE DRAWINGS

In FIG. 1, an ultrasonic applicator 1', which is improved through the subject of the aforementioned prior patent application, consists of e.g. a number $n'=108$ of individual transducer elements W1' through Wn' which are adjacently supported in a row 2' on a carrier section 3'. Carrier section 3' consists of a material which readily absorbs the ultrasound e.g. epoxy resin. Accordingly, in the operating state, ultrasonic radiation proceeds only in the directions of directional arrow 4' perpendicular to the application surface 5' of applicator 1'. Transducer elements W1' through Wn' of this ultrasonic applicator 1' are preferably small piezoelectric crystal plates manifesting a thickness $d=0.5$ mm, a width $b=0.9$ mm, and a length $l=8$ mm for operating frequencies e.g. in the range of approximately 4 MHz. The gap width s between the individual small transducer plates is set at $s=0.1$ mm. Thus, a raster distance (or screen line distance) of $r=1$ mm results. Given a total number of transducer elements $n'=108$, the entire length of the applicator 1' is $L=108$ mm. Upon actuating the transducer elements e.g. in four bit groups (or quadruplets) as well as forward clock pulsing by one transducer element with each clock pulse, respectively, there is a resulting line number of approximately 105 lines per ultrasonic image (the lines for the first two elements W1', W2', and the last two elements Wn'-1, Wn', of the transducer row are suppressed, since preferably only complete quadruplets (or four bit groups) are to contribute to the line formation. In the case of ultrasonic applicator 1 according to FIG. 2 of the aforementioned prior patent application, piezoelectric crystal plates again act as transducer elements W1 through Wn, which are correspondingly adjacently arranged in row 2 on a carrier section 3. Carrier section 3 is constructed according to that of FIG. 1, such that there is again a resulting radiation direction 4 which is perpendicular to the application surface 5 of applicator 1. The crystal plates W1 through Wn of transducer row 2 have a thickness $d=0.5$ mm and a length $l=8$ mm, corresponding to the small crystal plates W1' through Wn' of transducer 2' of applicator 1'. However, in contrast with the small crystal plates W1' through Wn', the width of the crystal plates W1 through Wn is twice as great; i.e., $2b=1.8$ mm. The gap spacing is correspondingly enlarged; i.e., it amounts to e.g. $2s=0.2$ mm. The raster distance of the plates is thus also doubled; i.e., $2r=2$ mm. Given an overall length of applicator 1 of again approximately $L=108$ mm, there is thus a resulting total number of the required transducer elements of $n=54$. However, in spite of the fact that there is only half the number of transducers, with the applicator 1 according to FIG. 2, there again results approximately the same line number as also in the case of the applicator according to FIG. 1; i.e., in precise terms, 101 lines per complete ultrasonic image with a stipulated four bit (or quadruplet) or five bit (or quintuplet) shift rhythm, such as shall be further explained in the following on the basis of FIG. 3.

In FIG. 3, ultrasonic applicator 1 is constructed corresponding to that of FIG. 2; i.e., it again comprises a transducer row 2 with a total of preferably 54 transducer elements. However, only the first seven transducer elements W1 through W7, as well as the n-th (i.e., the 54th) transducer element Wn, are illustrated. A number of actuating switches S1 through Sn, corresponding to the number of transducer elements, of a switch bank 6 serves the purpose of actuating the individual transducer elements W1 through Wn of transducer row 2. Each switch S1 through Sn, in the closed state, connects the respective transducer element W1 through Wn, associated with it, to a high frequency pulse transmitter 7 in the transmitting operation (or transmit mode) or to an echo signal receiver 8 in the receiving operation (or receiving mode). A display unit 9 serves the purpose of rendering visible the echo signals in the form of an echo sectional image; this display unit 9 being, for example, an electron beam tube (or cathode ray tube) which effects the image-formation of the echo signals arriving in line-by-line fashion from the subject under examination, said image-formation proceeding in a correspondingly linear fashion by means of light intensity modulation as bright spots on a display screen. In the apparatus according to FIG. 3, according to the aforementioned prior patent application, the continuous excitation of the transducer elements in groups of e.g. alternately four and five transducer elements takes place. Accordingly, the sample embodiment according to FIG. 3 thus comprises a total of two shift registers 10 and 11 with one associated group program transmitter 12, or 13, each. Group program transmitter 12 is adjusted such that, at the beginning of each scanning, it delivers to shift register 10 a four bit group (or quadruplet) of set pulses, respectively, which are then always further shifted (or advanced) by one register location in shift register 10 at the shift clock pulse rate of a central clock pulse control generator 14. Shift clock pulse line 15 serves the purpose of supplying the shift clock pulses of the clock pulse control generator 14 to shift register 10. In a corresponding fashion, group program transmitter 13 produces a five bit group (or quintuplet) of individual pulses, respectively, for shift register 11, which, in turn, are further shifted (or advanced) by one position, respectively, in shift register 11 at the clock pulse rate of the shift clock pulses of clock pulse control generator 14 which are supplied to shift register 11 via shift clock pulse line 16. The group program transmitters 12 or 13, respectively, can be readily reprogrammed, such that, instead of a four bit and five bit group combination, different-numbered group combinations — e.g. groups of two and groups of three, or the like — can also be easily randomly preselected. The actuation of the individual switches S1 through Sn of the switch bank 6 proceeds in dependence upon the output signals of shift registers 10 or 11, respectively, via a gate logic 17 which always connects the shift register outputs A1 through An of the respective shift register 10 or 11 to the control inputs of switches S1 through Sn when through-connection pulses of the clock pulse control generator 14 are conveyed to gate logic 17 via switching inputs 18 or 19, respectively. The gate logic 17 is so conceived here that, with the occurrence of a through-connection pulse on through-connection input 18, shift register 10 is connected at its output side to the control inputs of switches S1 through Sn, whereas, with the occurrence of the through-connection pulse on through-connection input 19 of gate logic 17, on the other hand, a connection is established between the control inputs of the switches and the signal outputs of shift register 11. As previously indicated, the respective through-connection pulses for gate logic 17 are supplied by the clock pulse control generator 14. Correspondingly, the clock pulse generator 14 also generates reset pulses for shift registers 10 or 11, respectively, via reset lines 20, or 21, respectively, as soon as the end of a complete pulsing cycle of the pulse groups through the respective shift registers 10 or 11, respectively, is acknowledged (or communicated back) via answerback (or acknowledgment signal) lines 22 or 23, respectively. Control lines 24 and 25 supply pulse transmitter 7 and display unit 9 with control signals of the clock pulse generator 14 for the transmitting/receiving cycles; i.e., for the echo-image formation. As previously indicated, in the basic circuit diagram according to FIG. 3, in the embodiment and according to the control (or operating) pattern of the aforementioned prior patent application, the forward switching of the transducer elements W1 through Wn proceeds in a step-by-step fashion alternating in four bit groups and five bit groups. The initiation of each scanning is thus determined such that a control pulse is delivered by the clock pulse control generator 14 to the group program transmitter 12 which subsequently counts into shift register 10 a combination consisting of four individual pulses. As soon as this counting-in operation has been terminated, a through-connection pulse is supplied by the clock pulse control generator 14 to the gate logic 17 via the through-connection input 18. This through-connection pulse connects outputs A1 through An of shift register 10 to the control inputs for the switches S1 through Sn. Since, in the case of shift register 10, only the first four outputs A1 through A4 are set, accordingly only switches S1 through S4 are closed. Via control line 24, pulse transmitter 7 is activated for the purpose of generating a high frequency pulse. This high frequency pulse is delivered via the closed switches S1 through S4 to transducer elements W1 through W4. The latter are energized in equiphase fashion, and an ultrasonic pulse is radiated which scans a (non-illustrated) subject under examination in a scan line corresponding to directional arrow Z1. Up to this point, the apparatus according to FIG. 3 corresponds in the method of operation to that of FIG. 3 of the prior patent application. In accordance with the inventive modification of the sample embodiment of FIG. 3, however, a transmitting/receiving group switch 27 is now provided as an additional component which, immediately following radiation of the first transmit pulse, switches over the central clock pulse control generator 14 via control line 28 in such a manner that switches S1 through S4 are opened again via switch bank 17, and group program transmitter 13 is simultaneously activated, which subsequently counts into shift register 11 a group of five individual pulses. As soon as this counting-in operation has been terminated, there is conveyed, via through-connection input 19, to the gate logic 17 an additional through-connection pulse which now connects the outputs A1 through An of shift register 11 to the control inputs of switches S1 through Sn. Since, of all outputs A1 through An of shift register 11, only outputs A1 through A5 are set, switches S1 through S5 are thus now closed. The echo signals of the transmit pulses of the preceding group (four transducer elements) are now, following conversion into corresponding electric signals by means of transducers W1 through W5, delivered via switches S1 through S5 to the echo signal receiver 8, and from there, are conveyed to the display unit 9 for recording in the form of a corresponding echo signal line. Prior to the forward switching to the next transducer group, the pulse transmitter 7 is again activated via control line 24 for the purpose of releasing an additional high frequency pulse. On account of this high frequency pulse, the transducer elements W1 through W5 are now simultaneously activated in an equiphase fashion. An ultrasonic scan pulse results which now scans the examination subject in a line direction Z2. The direction of this arrow Z2 thus runs through the center of transducer element W3. At the end of the second transmit pulse, the through-connection pulse on the through-connection line 19 again disappears, controlled via the transmitting/receiving group switch 27. Switches S1 through S5 are thus opened. Simultaneously, through clock pulse control generator 14, a clock pulse is conveyed to the shift clock pulse input 15 of shift register 10. The four bit pulse group (or quadruplet pulse group) located in shift register 10 is thereby forward-pulsed by one register location. At the end of this clock pulsing operation, there follows a repeated release of a through-connection pulse via the through-connection line 18 to gate logic 17. Outputs A1 through An of shift register 10 are thus again connected to the control inputs of switches S1 through Sn. However, since now only the outputs A2 through A5 of shift register 10 are set, only switches S2 through S5 are accordingly closed. The echo signals received from line Z2 with this new four bit group of tranducers W2 through W5 are again delivered via echo receiver 8 to the display apparatus 9 for the purpose of visual representation. Via the started pulse transmitter 7, there results, subsequent to the receiving cycle, excitation of transducer elements W2 through W5 and line scanning in the direction of line arrow Z3. With the termination of this third receiving/transmitting operation, further (or advance) pulsation of the five bit pulse group in shift register 11 takes place, likewise by one register location. The repeated through-connection of the gate logic 17 via the through-connection input 19 closes switches S2 through S6, such that excitation of transducer elements W2 through W6 and hence line scanning in the direction of line arrow Z4 results. The described cycle; i.e., alternate forward (or advance) pulsation of the four bit pulse group in shift register 10, or of the five bit pulse group in shift register 11, as well as subsequent corresponding through-connection of gate logic 17, is repeated until, in the case of shift register 10, the four bit pulse group, and, in the case of shift register 11, the five bit pulse group, each reach the output 22 or 23 of shift register 10 or 11, respectively. In this instance, the scan operation is terminated with the activation of the last four, or the last five, respectively, transducer elements of transducer row 2 of applicator 1, shift registers 10 or 11, respectively, are reset, and the scan operation is resumed again from the beginning by renewed insertion of pulses into shift register 10, or 11, respectively, and renewed resumption of the cyclical forward (or advance) pulsing. As indicated in FIG. 3, the result of this periodically progressive scanning is a scan line field 26 consisting of scan lines whose mutual spacings from one another corresponds in each instance to half the raster width of the transducer elements W1 through Wn. Thus, given a number of n=54 transducer elements, there is a resulting line raster (or line scanning pattern) for each ultrasonic image which is constructed from a total of $2(n-4)+1=101$ lines. Thus, with half the number of transducer elements as compared with conventional ultrasonic applicators, substantially the same number of lines results.

The new scanning pattern thus resulting which guarantees, for homogeneous structures, a constant for uniform) light intensity of the echo lines on the image screen of a cathode ray tube is illustrated in the basic diagram of FIG. 4. The letters n and n+1 here illustrate the switching-over rhythm between even-numbered and odd-numbered groups of the transducer element row W1 through Wn. The brackets in FIG. 4 arranged alongside at the right bearing the designations SE1 through SE6 indicate the transmitting/receiving cycles of active transducer groups in chronologically successive interlacing. The vertical lines illustrated at the bottom of FIG. 4 are the line-field of lines Z1 through Zn of the ultrasonic scan field for echo image lines of equal light intensity on the viewing screen of the oscilloscope tube. FIG. 5 illustrates the transmitting/receiving cycles with transmit pulses Sn and receiving groups with n+1 transducer elements for the echo signals (En) of each transmit pulse Sn, or with transmit pulses $S_{n+1}$, respectively, with which are associated transducer groups consisting of n-elements acting as the receiver for the echo pulses ($E_{n+1}$) of the transmit pulses $S_{n+1}$.

Figure 1:
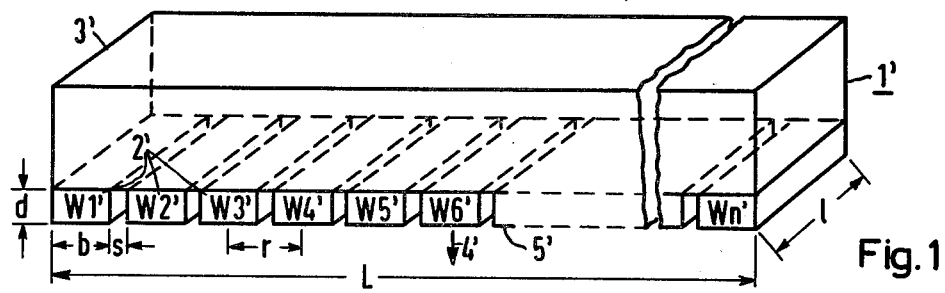
FIGS. 1 and 2 are diagrammatically partial perspective views showing ultrasonic applicators in an embodiment according to the aforementioned prior patent application.
Figure 2:
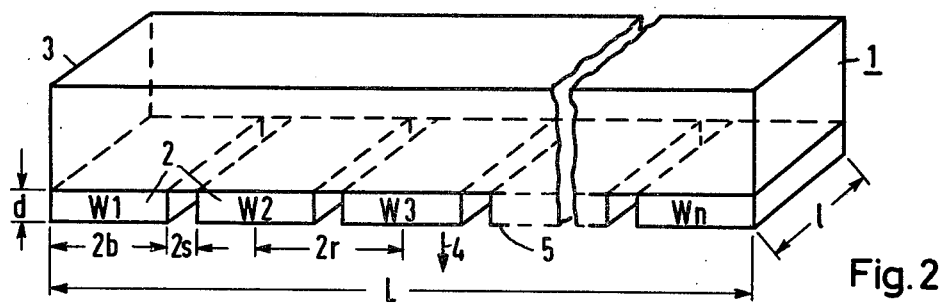
Figure 3:
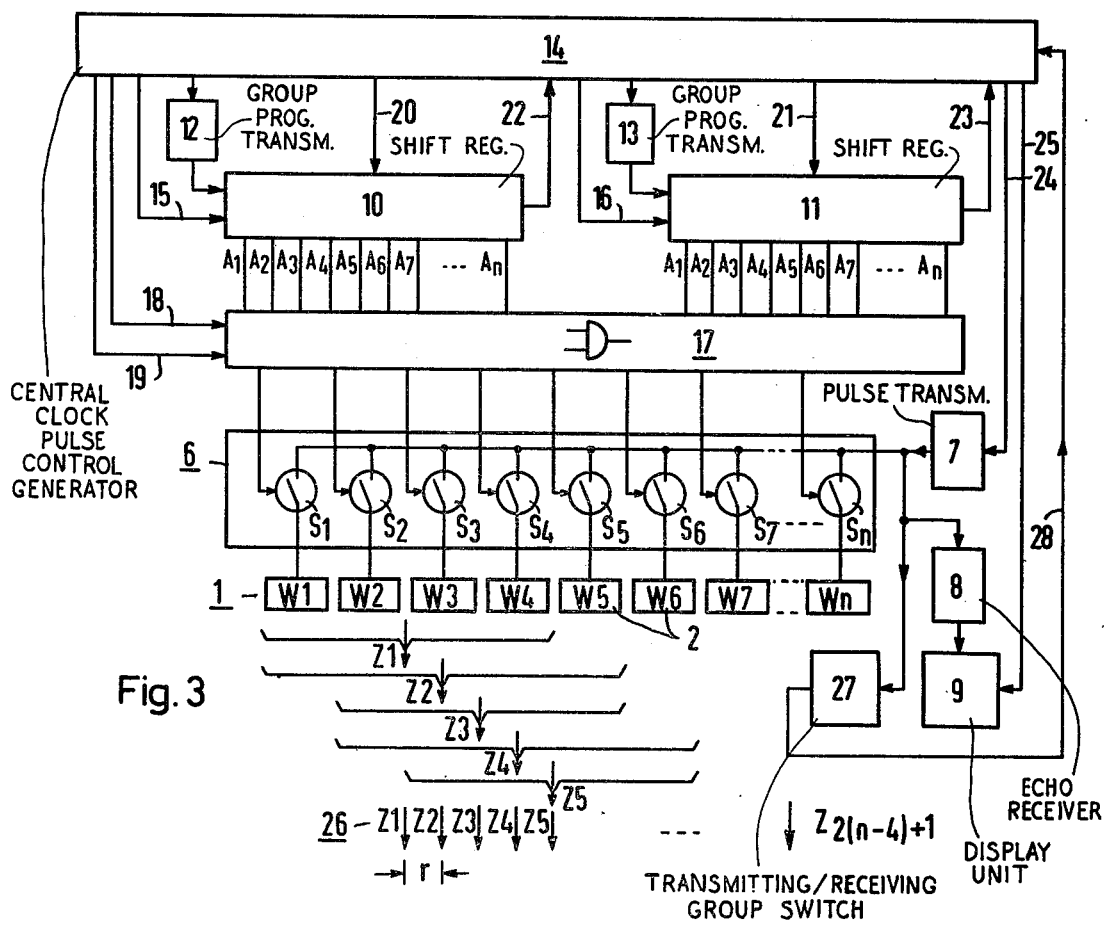
FIG. 3 shows a basic circuit diagram according to the prior patent application which is modified in accordance with the invention by a transmitting/receiving group switch for the purpose of sequential switching the scan operation and the line scan rate.
Figure 4:
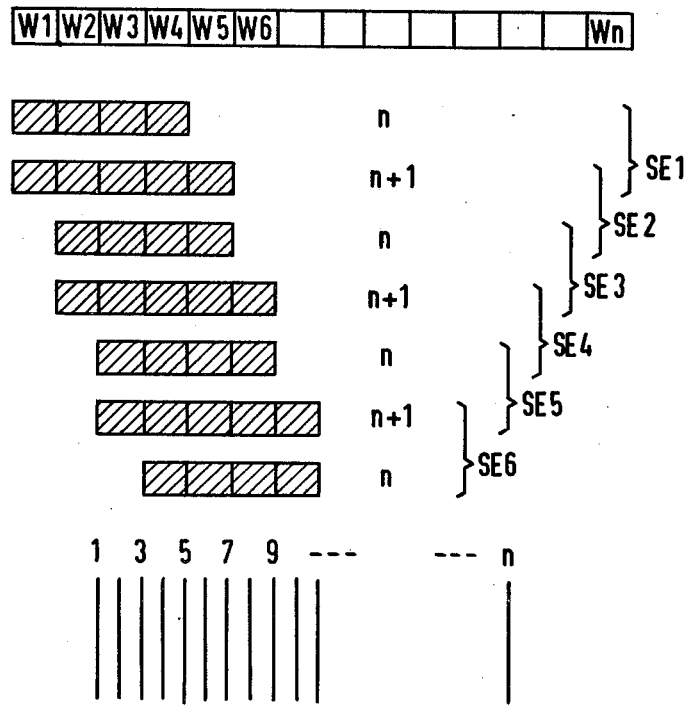
FIG. 4 illustrates the actuating pattern such as is obtained in a modified form with the modified actuating system according to FIG. 3.
Figure 5:
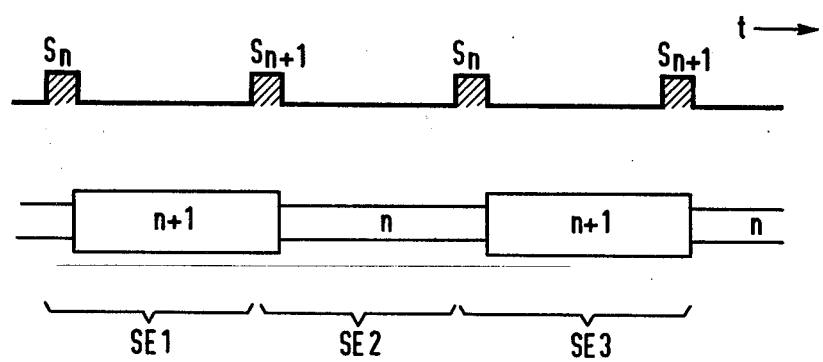
FIG. 5 illustrates the transmitting/receiving diagram in the case of an actuating pattern according to FIG. 4.

It will be apparent that many modifications and variations may be effected without departing from the scope of the novel concepts and teachings of the present invention.

I claim as my invention:

1. Apparatus for examining bodies through scanning by means of ultrasound comprising an ultrasonic applicator comprising at least one row of adjacently arranged ultrasonic transducer elements and an actuating system for group-actuation of the transducer elements, whereby the actuating system for actuating the transducer elements of the ultrasonic applicator is constructed in such symmetrical configurations with an even-numbered and odd-numbered count of transducer elements that the symmetry axes of the configurations of simultaneously energized transducer elements, at one time, become placed in the gaps between the adjacent transducer elements, and, another time, in the centers of the transducer elements, whereby the actuation proceeds in such a manner that, during a scan cycle over the entire length of the applicator, the symmetry axes occupy, at least once, every possible position in the gaps between two transducer elements, or in the centers of the transducer elements, respectively, with the possible exception of only the transducer elements of the first half of the first, and the second half of the last transducer element group of the applicator, characterized in that, the actuating system (6; 10 through 25; 27, 28), in an interlaced transmitting/receiving clock pulse sequence activates groups with an even-numbered and groups with an odd-numbered count of transducer elements (W1 through Wn) in a chronologically interlaced fashion such that each connected even-numbered or odd-numbered group, in relation to the previously connected group, in a first clock pulse interval, acts first as a receiver for the echo signals of the transmitting beam of the preceding group, and in a following clock pulse interval, is switched over to transmission.

2. Apparatus according to claim 1, characterized in that the actuating system alternately connects, in a chronologically interlaced fashion, groups with an even-numbered and groups with an odd-numbered count of transducer elements, whereby each connected even-numbered or odd-numbered group, in relation to the previously connected odd-numbered or even-numbered group, respectively, acts first as a receiver and then again as a transmitter.

3. Apparatus according to claim 1, characterized in that, in the case of even-numbered groups with n transducer elements and odd-numbered groups with (n+a) transducer elements, pursuant to transmission from a group with n transducer elements, directly following transmission of the transmit pulse, a group with (n+a) transducer elements is switched by the actuating system to reception for the echo signals of the transmit pulse of the n-group, or, conversely, during transmission of the transmit pulse by an (n+a)-group, an n-group is switched to reception, respectively, by the actuating system.

4. Apparatus according to claim 2, characterized in that, in the case of even-numbered groups with n transducer elements and odd-numbered groups with (n+a) transducer elements, pursuant to transmission from a group with n transducer elements, directly following transmission of the transmit pulse, a group with (n+a) transducer elements is switched by the actuating system to reception for the echo signals of the transmit pulse of the n-group, or, conversely, during transmission of the transmit pulse by an (n+a)-group, an n-group, is switched to reception, respectively, by the actuating system.

5. Apparatus according to claim 3, characterized in that, during switching-over from transmission to reception from an n-group to an (n+a)-group, a number a additional transducer elements are connected to the n-transmission group, or, during switching-over from transmission to reception from an (n+a)-group to an n-group, respectively, a number a of the transducer elements are correspondingly disconnected again, and the (n+a)-group, or n-group, respectively, form the receiving group or the respective following transmission group.

6. Apparatus according to claim 3, characterized in that, given an arbitrarily specifiable number n of transducer elements of an even-numbered group, the number of the odd-numbered group, in relation to the number n, is in each instance preferably always enlarged by one individual transducer element (a=1).

7. Apparatus according to claim 4, characterized in that, given an arbitrarily specifiable number n of transducer elements of an even-numbered group, the number of the odd-numbered group, in relation to the number n, is in each instance preferably always enlarged by one individual transducer element (a=1).

8. Apparatus according to claim 5, characterized in that, given an arbitrarily specifiable number n of transducer elements of an even-numbered group, the number of the odd-numbered group, in relation to the number n, is in each instance preferably always enlarged by one individual transducer (a=(a 1).

* * * * *